United States Patent
Guederian (10) Patent No.: US 10,117,657 B2
(45) Date of Patent: Nov. 6, 2018

(54) NAUTILUS GLENOID REAMER

(71) Applicant: Arthrex, Inc., Naples, FL (US)

(72) Inventor: Gregory A. Guederian, Naples, FL (US)

(73) Assignee: Arthrex, Inc., Naples, FL (US)

( * ) Notice: Subject to any disclaimer, the term of this patent is extended or adjusted under 35 U.S.C. 154(b) by 733 days.

(21) Appl. No.: 14/659,290

(22) Filed: Mar. 16, 2015

(65) Prior Publication Data
US 2015/0265288 A1 Sep. 24, 2015

Related U.S. Application Data (60) Provisional application No. 61/968,708, filed on Mar. 21, 2014.

(51) Int. Cl.
*A61B 17/16* (2006.01)

(52) U.S. Cl.
CPC ...... *A61B 17/1684* (2013.01); *A61B 17/1615* (2013.01)

(58) Field of Classification Search
CPC .. A61F 2/46; A61F 2/4609; A61B 17/320725; A61B 17/320758; A61B 17/1684; B23C 5/02; B23C 5/10; B27C 5/10; B23B 5/00
USPC ........................................ 30/352; 15/104.02
See application file for complete search history.

(56) References Cited

U.S. PATENT DOCUMENTS

| | | | |
|---|---|---|---|
| 2,785,673 A * | 3/1957 | Anderson | A61B 17/1666 606/81 |
| 4,252,481 A * | 2/1981 | Krieg | B23D 79/021 407/57 |
| 5,101,875 A * | 4/1992 | Eckhold | B23Q 9/0014 409/182 |
| 5,376,092 A | 12/1994 | Hein et al. | |
| 5,611,801 A * | 3/1997 | Songer | A61B 17/82 606/103 |
| 6,673,115 B2 | 1/2004 | Resch et al. | |
| 8,523,867 B2 | 9/2013 | Rauscher et al. | |
| 8,709,012 B2 | 4/2014 | Muller | |
| 2008/0306482 A1 | 12/2008 | Muller | |
| 2011/0015636 A1* | 1/2011 | Katrana | A61B 17/15 606/87 |
| 2011/0028977 A1 | 2/2011 | Rauscher et al. | |
| 2012/0239042 A1 | 9/2012 | Lappin et al. | |

(Continued)

FOREIGN PATENT DOCUMENTS

| | | | | |
|---|---|---|---|---|
| DE | 3404123 A1 | 6/1985 | | |
| EP | 2 481 361 A1 | 8/2012 | | |
| GB | 540073 A * | 10/1941 | ........... | B23B 51/009 |

*Primary Examiner* — Brian Pellegrino
(74) *Attorney, Agent, or Firm* — Blank Rome LLP (57) ABSTRACT

Apparatus and methods for preparing a bone socket, such as the glenoid of the scapula, to receive a prosthetic component. The apparatus is an orthopedic instrument (reamer) used for the preparation of bone surface for the insertion of an implant. The reamer includes an elongate shaft, a connecting system (for example, a quick connect system), and a cutting head having a specific configuration, i.e., in the shape of a Nautilus shell having a logarithmic spiral. The cutting head is provided with a plurality of spokes that have different radii or lengths (that confer a non-constant non-uniform radius to the overall cutting head).

12 Claims, 10 Drawing Sheets

(56) References Cited

U.S. PATENT DOCUMENTS

2012/0323247 A1* 12/2012 Bettenga ................ A61F 2/46
  606/91
2013/0150859 A1   6/2013 Kehres et al.

\* cited by examiner

NAUTILUS GLENOID REAMER

CROSS-REFERENCE TO RELATED APPLICATIONS

This application claims the benefit of U.S. Provisional Application No. 61/968,708, filed Mar. 21, 2014, the entire disclosure of which is incorporated by reference herein.

BACKGROUND OF THE INVENTION

1. Field of the Invention

The present invention relates to methods and apparatus for surgical procedures.

2. Description of the Related Art

Reamers are used by surgeons to prepare bones for receiving components of artificial joints. For example, a glenoid reamer is used to prepare shoulder sockets for insertion of artificial shoulder joints. The dimensions and shape of the cavity cut are critical in many surgical procedures, as the tolerances between the cavity and the socket portion of a joint must be small to ensure proper function. This is especially true with the cementless prostheses, wherein the socket portion is frictionally fit into a cavity, placing added importance upon accurate cavity dimensions and tolerances.

It would be desirable to provide a glenoid reamer that allows reaming of the glenoid surface when there is difficult exposure, or when low profile insertion is needed. Also needed are methods of reaming the glenoid which promote displacement of the debris away from the cutting surface of a glenoid reamer as well as a better view of the surface for the surgeon when the exposure is limited or difficult.

SUMMARY OF THE INVENTION

The present invention provides apparatus and methods for preparing a bone socket, such as the glenoid of the scapula, to receive a prosthetic component.

The apparatus is an orthopedic instrument (reamer) used for the preparation of bone surface for the insertion of an implant. The reamer includes an elongate shaft, a connecting system (for example, a quick connect system), and a cutting head having a specific configuration, i.e., a Nautilus shell having a logarithmic spiral with a semicircle or quarter circle shape. The cutting head is provided with a plurality of spokes that have different radii or lengths (that confer a non-constant non-uniform radius to the overall cutting head).

These and other features and advantages of the invention will be more apparent from the following detailed description that is provided in connection with the accompanying drawings and illustrated exemplary embodiments of the invention.

DETAILED DESCRIPTION OF THE INVENTION

The present invention provides apparatus and methods for preparing a patient's bone with a cutting instrument (orthopedic reamer) having a cutting head with a specific shape and configuration, i.e., with a shape resembling that of a Nautilus shell. The orthopaedic reamer of the present invention may be employed for preparing a bone socket, for example, for preparing a bone socket in the glenoid to receive a prosthetic glenoid component.

The present invention provides apparatus and methods for preparing a bone socket, such as the glenoid of the scapula, to receive a prosthetic component.

The apparatus is an orthopedic instrument (reamer) used for the preparation of bone surface for the insertion of an implant. The reamer includes an elongate shaft, a connect system, and a cutting head having a specific configuration, i.e., in the shape of a Nautilus shell having a logarithmic spiral.

In an exemplary embodiment, the cutting head of the instrument is provided with slots that allow for the collection of debris and for the surgeon to be able to observe the surface being developed. These slots create a plurality of cutting spokes which have a spherical radius and a cutting edge that will conform to the posterior geometry of the implant. The cutting head has a half sphere design with a decreasing radius throughout the spokes, making each one shorter than the previous one.

The cutting head of the reamer is attached to the shaft. The shaft has a diameter smaller than that of the cutting head of the reamer. The shaft includes a connect system (for example, a quick connect system) on its end, in order to mate with a power tool. In an exemplary embodiment, both the shaft and the cutting head are cannulated, with a small peg located in the center of the cutting head. In additional embodiments, the shaft and the cutting head are not cannulated. The addition of both these features allows for the instrument to accommodate the surgeon's preference during the procedure.

In an additional embodiment, the reamer is integrally attached to a drill tip with a full cannulation to allow easy passage of another surgical instrument, for example, of a drill pin or similar device.

The present invention also provides a reamer, comprising inter alia: (i) a shaft with a longitudinal axis, a proximal end and a distal end; (ii) a cutting head provided at the distal end of the shaft, the cutting head being provided with a plurality of spokes/arms/blades extending radially away from the shaft and in a direction perpendicular to the longitudinal axis of the shaft, wherein each of the plurality of spokes/arms/blades has a radius/length different from radii/lengths of adjacent spokes/arms/blades; and (iii) a continuous base that connects most distal regions of all of the plurality of spokes/arms/blades. The cutting head has a shape of a Nautilus shell having a logarithmic spiral. At least one of the shaft and the cutting head may be fully cannulated. Each of the plurality of spokes/arms/blades has a cutting edge for cutting a bone and form a bone cut (bone socket) that resembles the geometry of an implant to be inserted in the bone cut (socket) formed by the reamer.

In additional embodiments, and as detailed below, the reamer may further comprise a drill tip adjacent the cutting head, the cutting head being disposed between the drill tip and the shaft, wherein the drill tip, the cutting head and the shaft are fully cannulated to allow another surgical instrument (such as a drill pin, for example) to pass therethrough. The drill tip may be integral to the cutting head, or may be interchangeable, i.e., removably attached to and detached from the cutting head.

The present invention also provides a method of preparing a glenoid of a patient's scapula to receive a prosthetic glenoid component, the method comprising inter alia the steps of: (i) providing a reamer having a shaft with a longitudinal axis, a proximal end and a distal end; a cannulated cutting head provided at the distal end of the shaft, the cutting head being provided with a plurality of spokes or blades or arms extending radially away from the shaft and in a direction perpendicular to the longitudinal axis of the shaft, and a base connecting the plurality of spokes; wherein each of the plurality of spokes has a length extending between the cannulation of the head and the base and characterized in each spoke has a length different from the length of all other remaining spokes; (ii) positioning the cutting head of the reamer against the glenoid; and (iii) removing bone from the glenoid. The method may further comprise the step of implanting/securing a glenoid component into the patient's scapula.

Referring now to the drawings, where like elements are designated by like reference numerals, FIGS. 1-9 illustrate exemplary orthopedic cutting instrument (reamer) 100, 200 of the present invention and securing mechanism 300 (in the form of a clamping or chuck mechanism) which may be employed with the reamers 100, 200. FIGS. 10-17 illustrate exemplary steps of a method of bone preparation with reamer 100 of the present invention, prior to receipt/insertion of an implant, and according to an exemplary embodiment of the present invention.

As detailed below, orthopedic cutting instrument (reamer) 100, 200 of the present invention may be used for the preparation of a bone surface for the insertion of an implant.

FIGS. 1-5 illustrate reamer 100 that includes an elongate shaft 10 rotatable about a longitudinal axis 10*a*, a connecting system 20 (for example, a quick connect system 20), and a cutting head 50 having a specific configuration, i.e., in the shape of a nautilus shell having a logarithmic spiral (Nautilus glenoid reamer). In an exemplary embodiment, the cutting head 50 has an overall configuration in the shape of a half of a hemisphere (a quarter of a sphere or a half moon), i.e., a half of a nautilus shell, as shown clearly in FIG. 1, for example. Longitudinal axis 10*a* of the shaft 10 extends through the centerline (longitudinal axis) of the cutting head 50.

Figure 3:
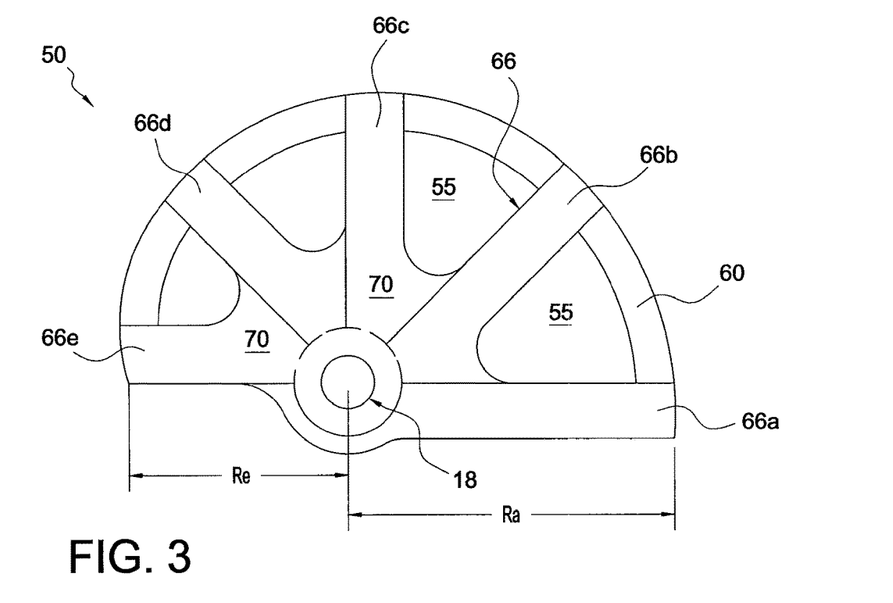
FIG. 3 is a top view of the cutting head of the reamer of FIG. 1.
Figure 4:
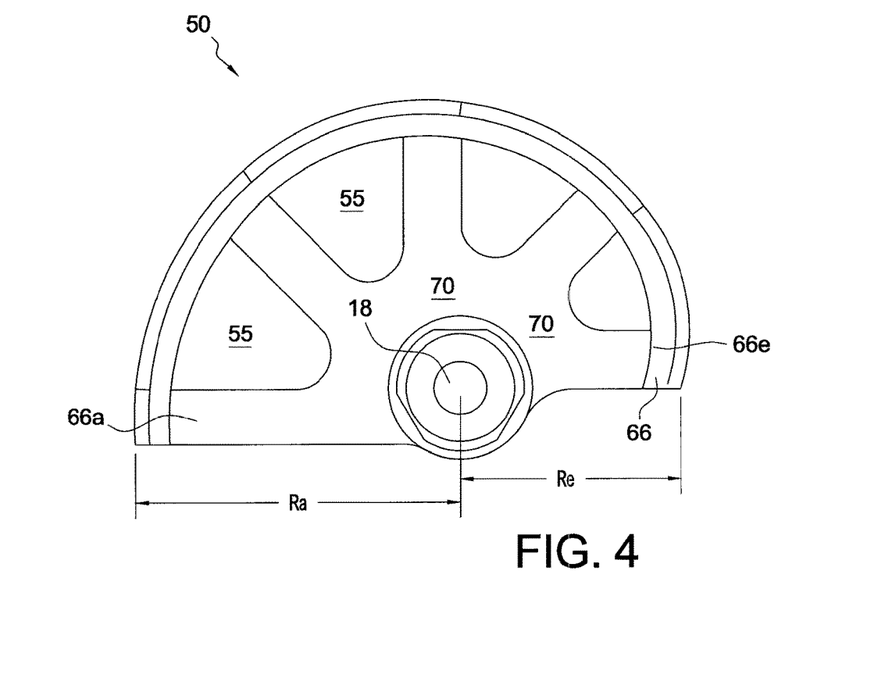
FIG. 4 is a bottom view of the cutting head of the reamer of FIG. 1.
Figure 5:
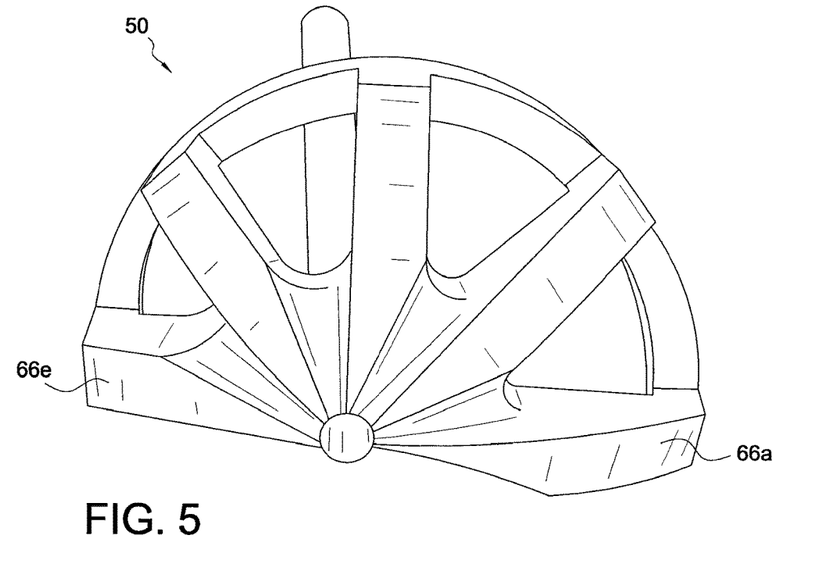
FIG. 5 is a perspective view of the cutting head of the reamer of FIG. 1.
Figure 6:
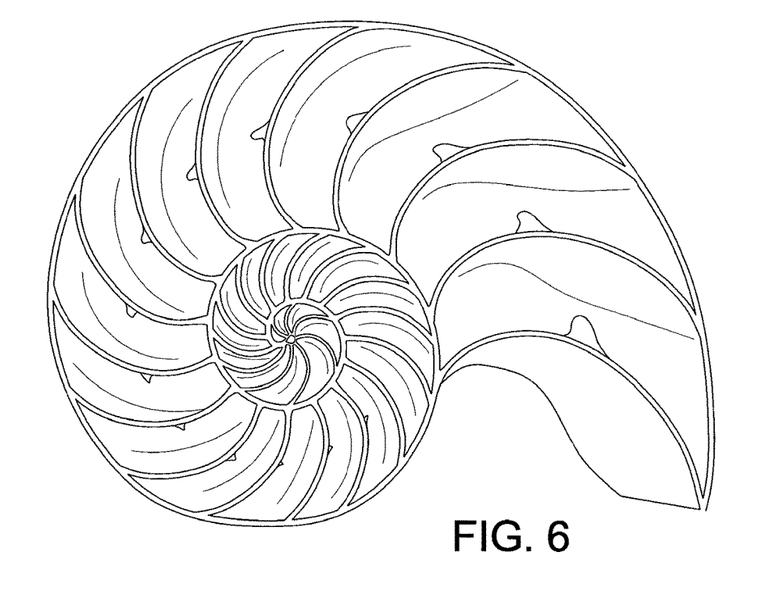
FIG. 6 is a cross-sectional view of a nautilus shell.

In an exemplary embodiment, the cutting head 50 of the instrument is provided with slots 55 (FIGS. 3 and 4) that allow for the collection of debris and for the surgeon to be able to observe the surface being developed. These slots create a plurality of cutting spokes 66*a*-66*e* (denoted generally as structure 66) or blades or cutting arms 66*a*-66*e* that project radially outwardly from the longitudinal axis 10*a* of the shaft and of the cutting head. Cutting spokes 66*a*-66*e* are all connected distally by a continuous, peripheral wall or base 60. Cutting spokes 66*a*-66*e* extend radially outwardly from the longitudinal axis 10*a* of the shaft 10 and of the cutting head 50, and toward the base 60. The longitudinal axis 10*a* of the shaft 10 is radially offset from the base 60, as best seen in FIGS. 3 and 4. Cutting spokes 66*a*-66*e* are also all connected proximally by regions 70 extending radially from cannulation 18 of the head 50 and connecting proximal adjacent regions of spokes 66*a*-66*e*.

Cutting spokes 66*a*-66*e* have an exemplary-only spherical radius and a cutting edge 69 that will conform to the posterior geometry of the implant. In an exemplary embodiment, each spoke 66*a*-66*e* is shorter than the previous spoke (i.e., has a radius/length shorter than the radius/length of the previous spoke).

The exemplary embodiment of FIGS. 1-5 illustrates five spokes 66*a*, 66*b*, 66*c*, 66*d* and 66*e*; however, the spokes may be provided in any number as long as the length/radius of the spokes increases or decreases gradually to confer the overall Nautilus shape of the head 55. Each spoke has a radius different from the adjacent spokes and from all remaining spokes. For example, and as shown clearly in FIGS. 3 and 4, spoke 66*a* has a radius/length Ra (the greatest radius/length of all spokes) which is greater than radius Rb of adjacent spoke 66*b*, which in turn is greater than radius Rc of spoke 66*c*, etc. and greater than radius Re of spoke 66*e* (the smallest radius/length of all spokes). The radius of each spoke is defined as the length of the spoke between the longitudinal axis 10*a* to the periphery surface of the cutting head 50, i.e., to the base 60. Radii Ra-Re gradually decrease from Ra to Re by a same difference delta between adjacent radii. All spokes have different lengths/radii, i.e., each of the spokes has a length/radius different from all remaining spokes.

The cutting head 50 may have a half sphere design/geometry with a decreasing radius throughout the spokes 66*a*-66*e*, making each spoke shorter than the previous one. The cutting spokes may have any other geometry, i.e., not a spherical radius, for example, they could be flat or have some other undetermined shape.

Figure 2:
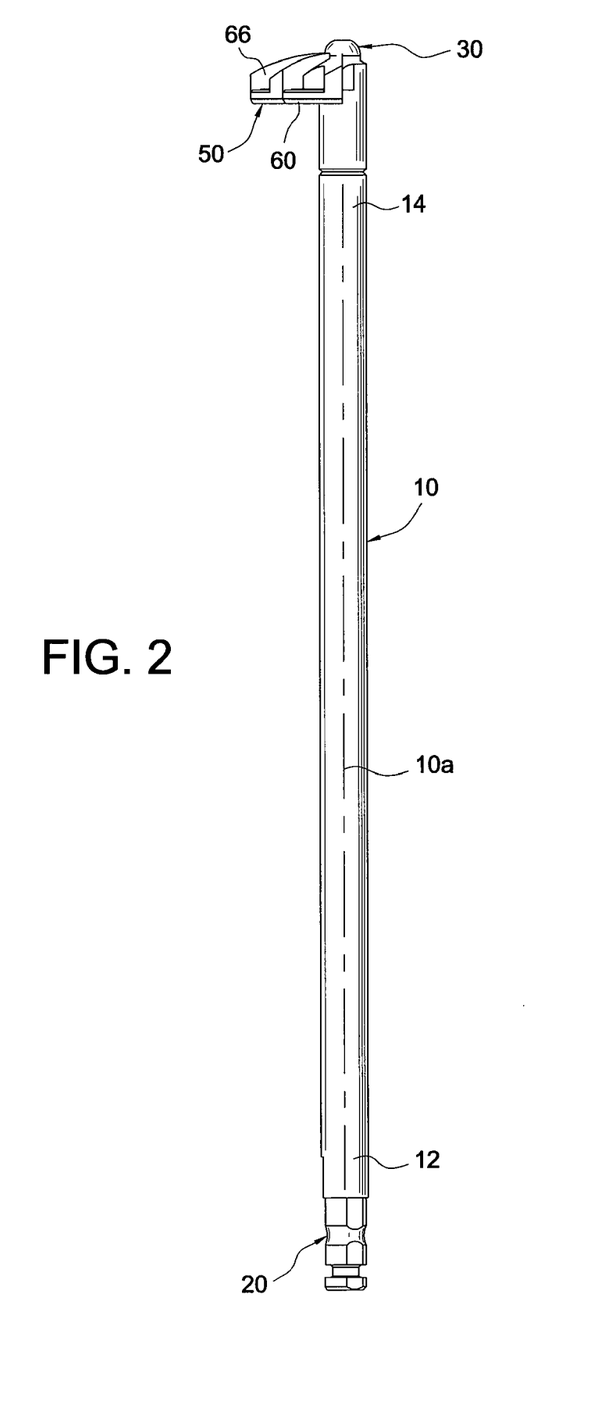
FIG. 2 illustrates a side view of the reamer of FIG. 1.

The cutting head 50 of the reamer 100 is attached to the shaft 10 at end 14. The shaft 10 has a diameter smaller than that of the cutting head 50 of the reamer. The shaft 10 also includes a connecting system 20 (for example, a quick connect system 20) on end 12 of the shaft 10, in order to mate with a power tool (not shown). In an exemplary embodiment, both the shaft 10 and the cutting head 50 are cannulated (provided with cannulation 18), with an optional small peg 30 (separate detachable "nub" component 30) located in the center of the cutting head 50 (as shown in FIG. 2, for example). The structures may be also non-cannulated. In additional embodiments, only one of the cutting head and shaft is cannulated. The addition of both of these features allows for the instrument 100 to accommodate the surgeon's preference during the procedure.

Figure 7:
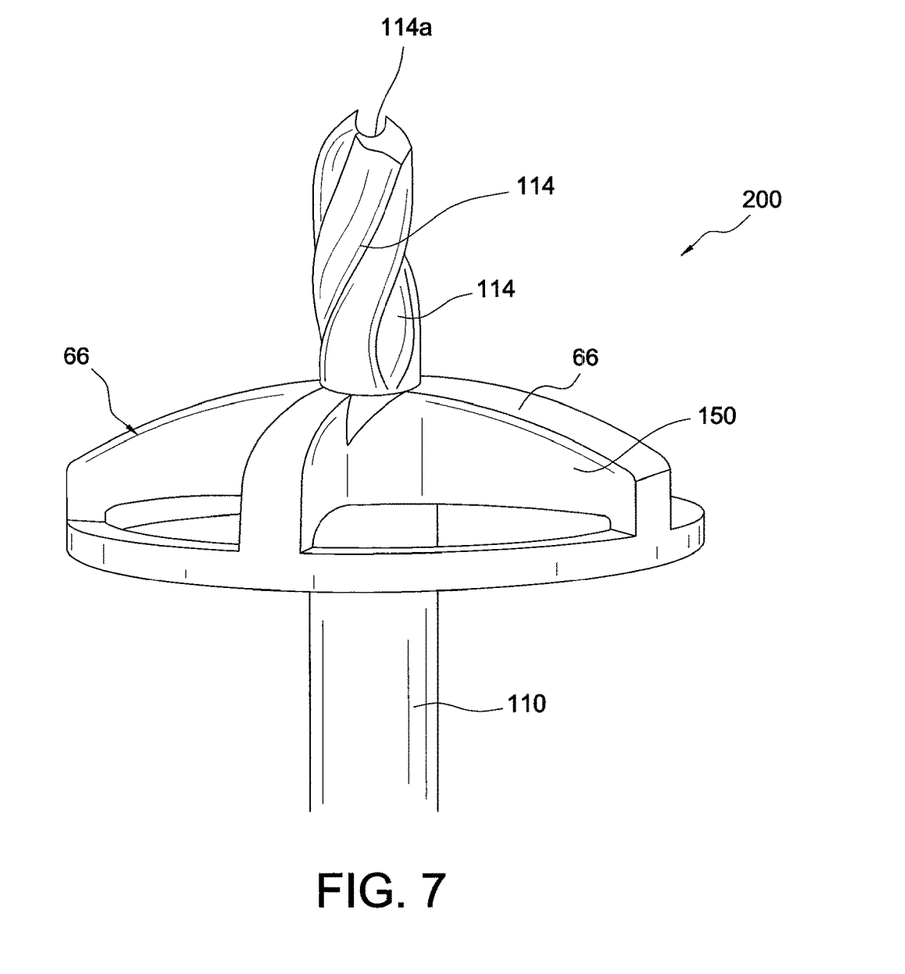
FIG. 7 illustrates a side view of an exemplary reamer of the present invention according to a second embodiment of the present invention.
Figure 8:
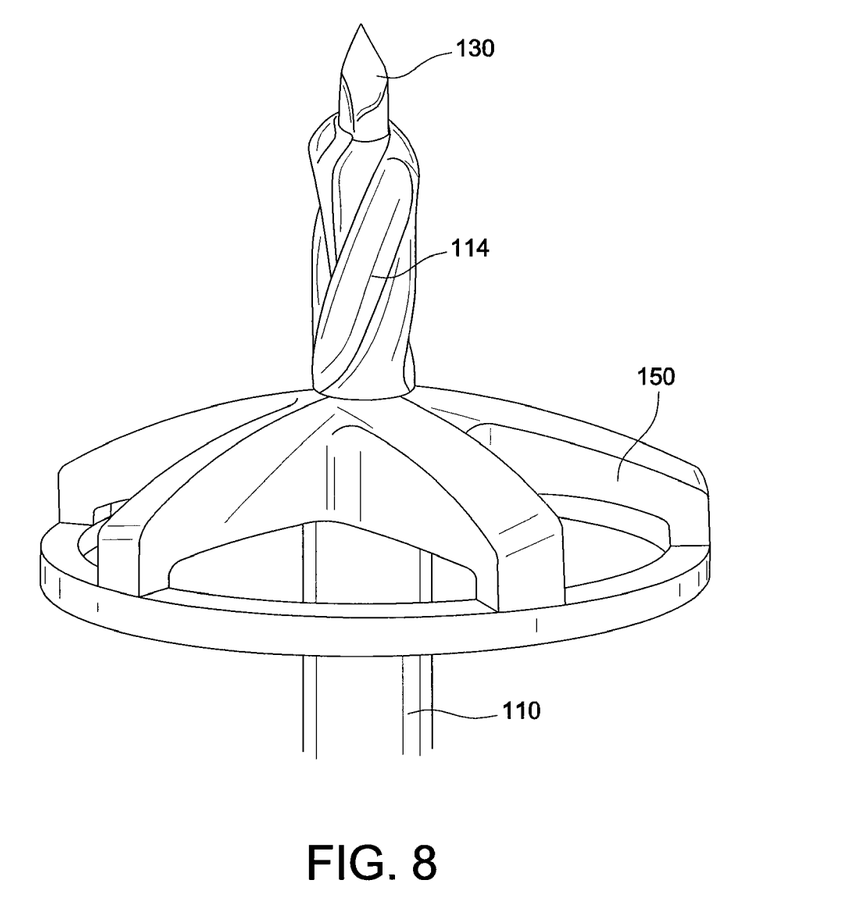
FIG. 8 illustrates the reamer of FIG. 7 with a cutting drill.

FIGS. 7-8 illustrate another exemplary glenoid reamer 200 of the present invention. Reamer 200 is a configuration variant of a reamer which features a cannulated drill tip. This drill tip is a drill that allows a drilling and subsequent reaming operation to occur without the requirement of utilizing two separate instruments. Both functions are combined into one homogenous device 200. Alternatively, the tip may be detachable and non-cannulated as well.

As shown in FIG. 7, reamer 200 is about similar to reamer 100 described above in that head 150 is about similar to head 50, but differs from it in that shaft 110 and cutting head 150 are integral with a most distal end 114 which is a cannulated drill (cannulated drill tip 114) that is provided above head 150. In an exemplary embodiment, distal drill tip 114 is fully cannulated to allow surgical instrument 130 (FIG. 8) to pass therethrough and aid in a cutting operation. FIG. 7 shows most distal opening 114a provided at the end of drill tip 114. In an exemplary only embodiment, surgical instrument 130 (FIG. 8) is a drill pin 130 that aids in the formation of a bone socket or tunnel.

Shaft 110 and/or cannulated drill tip may be provided pre-assembled to the cutting head 150 or may be secured to the cutting head 150 at the time of surgery. Shaft 110 and/or cannulated drill tip 114 may be integral to the cutting head, i.e., the whole instrument 200 is provided as a one piece formed by welding, for example, or by similar methods of attachment known in the art. In additional embodiments, the cannulated drill tip may be removably attached to and detached from the cutting head, by threading, for example. The components may be interchangeable or integrally attached to each other. In an exemplary embodiment, drill tip 114 may be non-cannulated.

Figure 1:
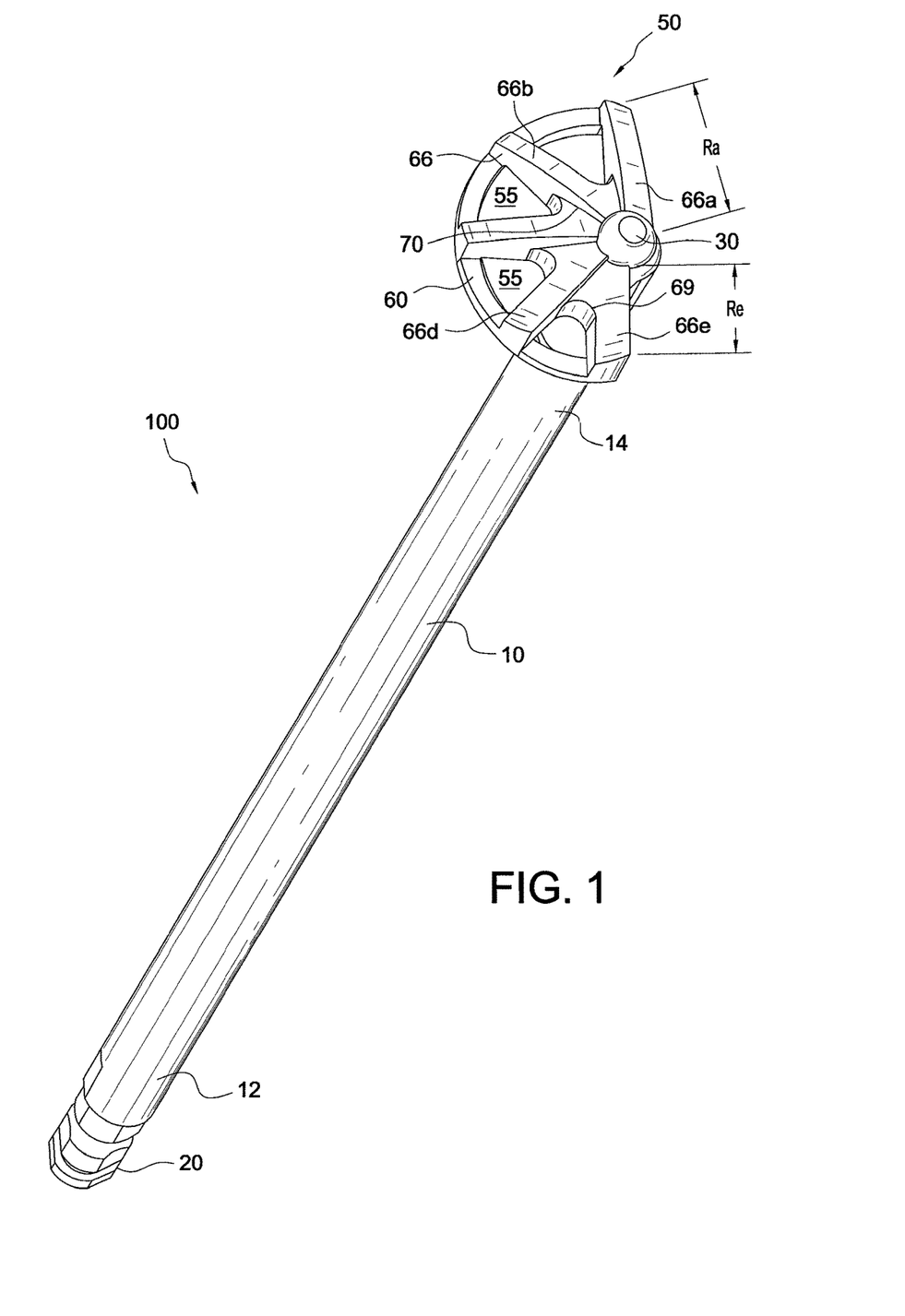
FIG. 1 illustrates a perspective view of an exemplary reamer of the present invention according to a first embodiment of the present invention.
Figure 9:
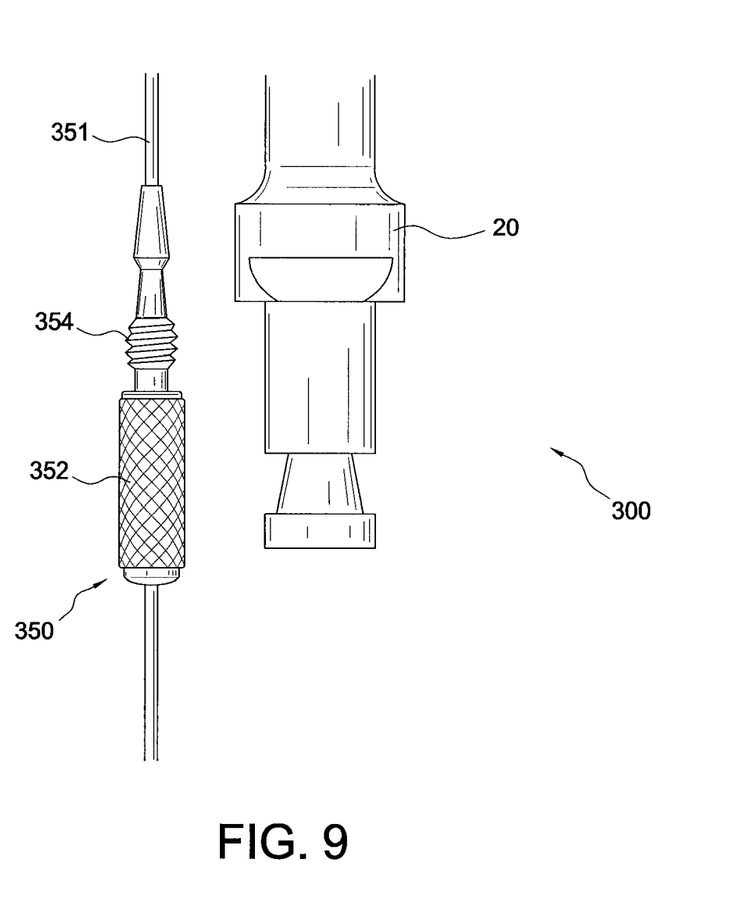
FIG. 9 illustrates an exemplary capturing mechanism for the reamer of FIG. 7.

FIG. 9 shows an exemplary type of securing/capturing mechanism 300, which may be a clamping or chuck mechanism 350 shown next to a connecting mechanism 20 (also shown in FIG. 1). Chuck 350 is provided with knurl 352, threaded region 354 and pin 351 that are all coupled together. Securing/capturing mechanism 300 may be employed in embodiments which do not employ pin 130 (shown in FIG. 8) passed through drill tip 114. When pin 130 is not used, securing/capturing mechanism 300 allows for pin 351 to be inserted and captured within the cannulation of the body (cannulation of shaft 110 of FIG. 7) and to close the cannulation, to provide stability of the reamer device 200 (to direct the drill tip 114) when the intent is to use the device in an unguided manner (such as shown in FIG. 7). The overall intent is for a pin to be captured and this can be accomplished numerous ways (and not limited to the clamping or chuck mechanism). This embodiment allows alternate components to capture and retain pin as part of the connector.

The Nautilus glenoid reamer 100, 200 of the present invention has at least three main characteristics that differentiate it from the known cutting reamers. The first difference consists in the semicircle or quarter circle form of the head 50, 150. With a smaller surface area occupied by the head, it is easier for the surgeon to manipulate the insertion of the instrument 100, 200 through a narrower, low profile incision.

Second, the overall diameter of the reamer 100, 200 decreases throughout the spokes 66. The small-to-large design does not jeopardize the desired outcome; on the contrary, it allows for easier and better functioning of the instrument 100, 200 in a tight cavity in which retractors occupy a high percentage of the working space. The design of the spokes 66 allows for the reamer 100, 200 to not only cut the center aspect of the bone surface, but also the outer edge. As the radius of the spokes increases, the radius of the cut, as well as the amount of bone removed, will also increase. Displacement of the debris away from the cutting surface is also promoted by the small-to-big feature. Additionally, the smaller spokes of the reamer will allow for a better view of the surface for the surgeon when the exposure is limited or difficult. The specific Nautilus shape also allows for smooth and transitional deflection of surgical instruments (for example, retractors) which are simultaneously located within the surgical site (wound).

Finally, the instrument 100 contains the cannulation 18 and the peg feature 30 incorporated in its design. These features allow for the instrument to be utilized in an assisted or non-assisted procedure. Instrument 200 contains cannulated drill tip 114 which allows drilling and subsequent reaming operations to occur without the requirement of utilizing two separate instruments. Both functions are combined into one homogenous device.

The glenoid reamer 100, 200 allows reaming of the glenoid surface when there is difficult exposure, or when low profile insertion is needed. The glenoid reamer 100, 200 may be employed in methods of reaming the glenoid promoting displacement of the debris away from the cutting surface of a glenoid reamer as well as a better view of the surface for the surgeon when the exposure is limited or difficult.

The present invention also provides a method for preparing a bone surface. In an exemplary-only embodiment, the invention provides a method of preparing the glenoid of a patient's scapula using orthopaedic reamer 100, 200 of the present invention. The method includes inter alia the steps of: (i) accessing the patient's scapula; (ii) positioning the cutting head 50, 150 of reamer 100, 200 against the glenoid; and (iii) forming a socket within the glenoid with cutting head 50, 150.

FIGS. 10-17 illustrate subsequent steps of a method of preparing a bone surface with the reamer 100, 200 of the present invention. Reamer 100, 200 may be provided as part of a set/kit and may be employed for exemplary total shoulder reconstruction.

Reamer 100, 200 may be part of Univers Nautilus Glenoid Reamer Set to the Univers II and Univers Apex Total Shoulder Systems. The Univers Nautilus Reamer System is a low profile cannulated option for initial glenoid surface preparation. The cannulation allows precise and stable glenoid surface preparation as well as version correction when necessary. The set contains glenoid sizing guides which have enlarged windows for optimal visualization of the entire glenoid surface.

The reamers and drill are cannulated for use over a 2.8 mm Steinmann Pin. The low profile "Nautilus" shaped cannulated reamers allow ease of passage of the cannulated shaft through the often narrow passage between retractors exposing the glenoid surface. The graduated radius of the reamer cutting surface minimizes the impact of the clockwise spinning reamer if it makes contact with a retractor.

The 2.8 mm Steinmann pin is available separately or in the Univers II/Eclipse Sterile Pin Set. If preferred, a shorter version of the 2.8 mm Steinmann pin is available in the Univers Revers Sterile Pin Set.

An exemplary surgical technique of the present invention is detailed below with reference to FIGS. 10-17 and utilizes reamer 100, 200 as part of the Univers Nautilus Reamer System, which is a low profile cannulated option for initial glenoid surface preparation prior to placing the keel and/or peg locations with the standard Univers #2 drill guides. The cannulation allows precise and stable glenoid surface preparation and version correction when necessary.

Figure 10:
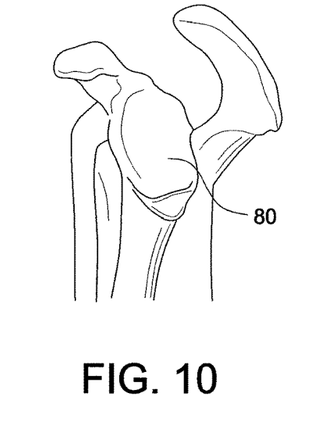
FIGS. 10-17 illustrate subsequent steps of a method of shoulder repair with the reamer of FIG. 1, and according to an exemplary embodiment of the present invention.

FIG. 10: Obtain complete exposure of the glenoid articular surface 80.

Figure 11:
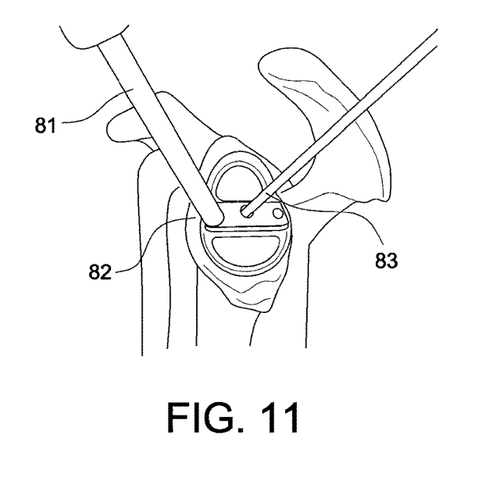

FIG. 11: Assemble the 2.8 mm glenoid pin guide 82 (which matches the glenoid surface area) to the glenoid guide handle 81. Drive the pin 83 through the glenoid vault until it reaches the medial vault cortical bone.

Figure 12:
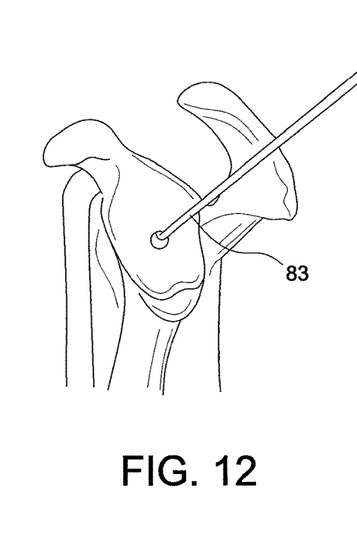

FIG. 12: Remove the guide and verify central glenoid pin 83 placement, as well as appropriate pin version and inclination.

Figure 13:
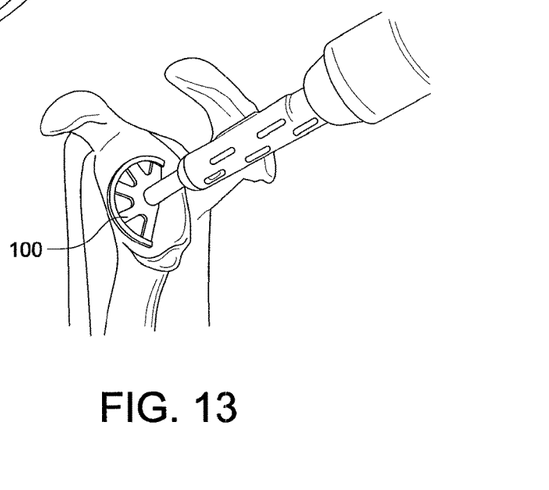

FIG. 13: Select the reamer size matching the glenoid pin guide size used in the previous step. Place the cannulated reamer 100 over the guide pin 83. Initiate the reamer before contacting the glenoid surface to minimize risk of glenoid rim fracture. The glenoid is reamed until the native surface is made congruent to the mating implant component backside geometry, to obtained reamed region 88 (FIG. 14).

Figures 14, 14A:
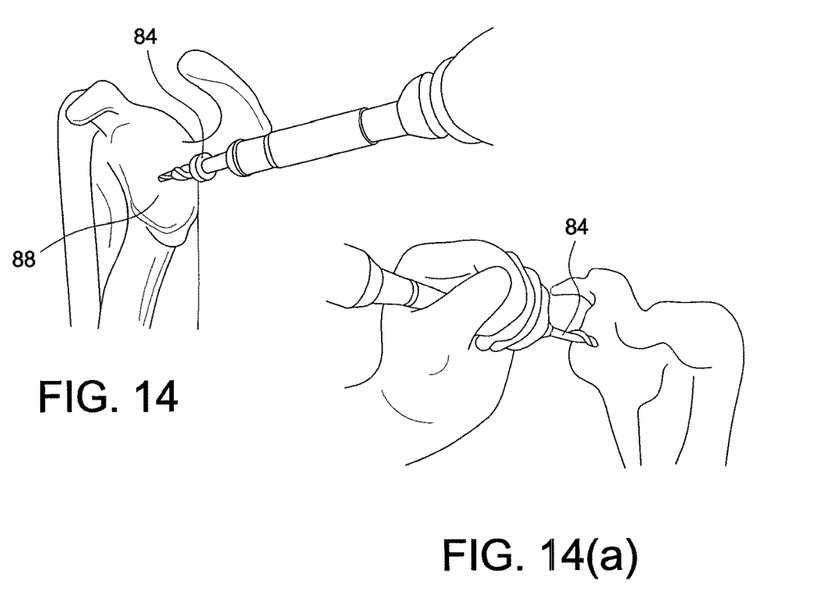

FIGS. 14 and 14(*a*): Place the cannulated 6 mm drill 84 over the guide pin and prepare the central keel/peg site. The drilling continues until the positive stop reaches the glenoid surface.

Figures 15, 15A:
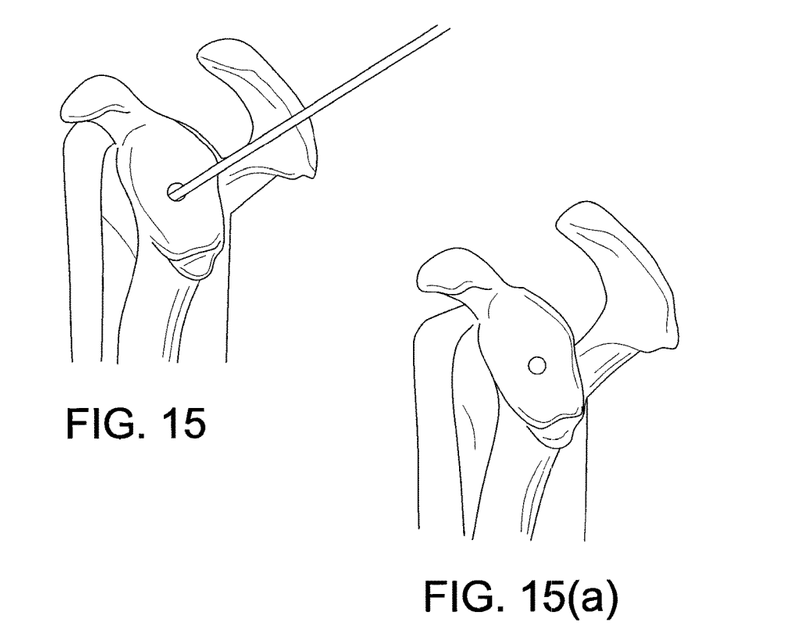

FIGS. 15 and 15(*a*): Remove the pin 83 and proceed to Drill Guide #2 (keeled or pegged) to complete glenoid preparation for the desired Keeled or Pegged implant respectively.

NOTE: The 6 mm cannulated drill is designed to prepare the central hole specifically. The non-cannulated 6 mm drills from the Univers II Instrument Set must be used to prepare the keel and superior peg sites through the respective keel and peg #2 drill guide.

Figure 16:
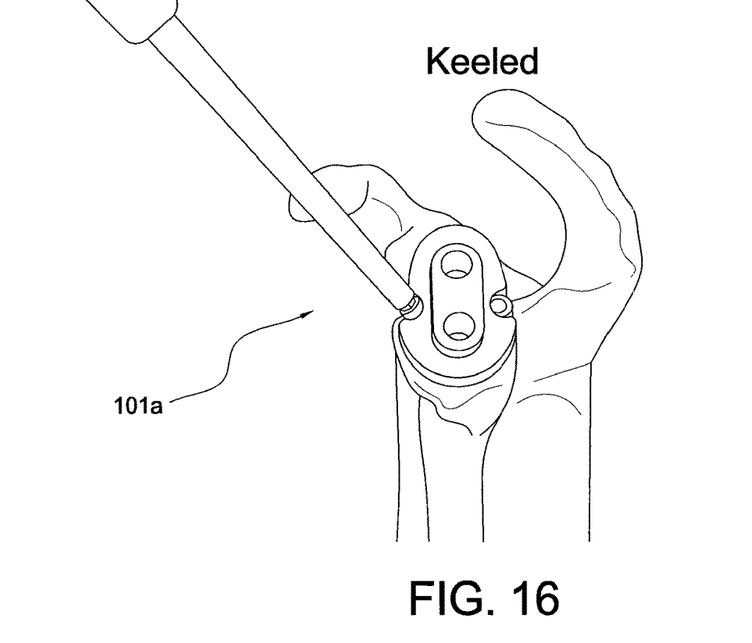

FIG. 16 shows a keeled embodiment 101*a*.

Figure 17:
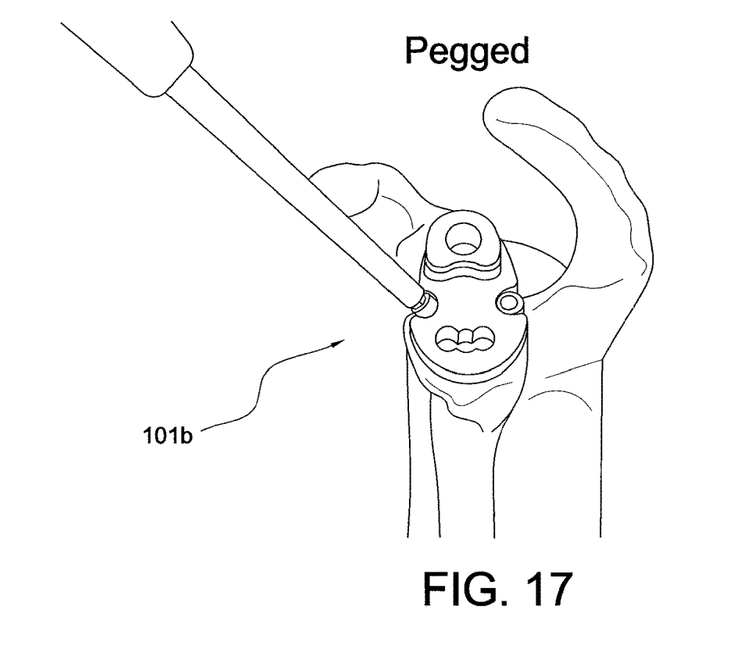

FIG. 17 shows a pegged embodiment 101*b*.

The Univers Nautilus Reamer Surgical Technique eliminates the need for the Univers II Drill Guide #1. Glenoid preparation continues with Drill Guide #2 from the Univers II Instrument Set.

Although the present invention has been described in connection with preferred embodiments, many modifications and variations will become apparent to those skilled in the art. While preferred embodiments of the invention have been described and illustrated above, it should be understood that these are exemplary of the invention and are not to be considered as limiting. Accordingly, it is not intended that the present invention be limited to the illustrated embodiments, but only by the appended claims.

What is claimed as new and desired to be protected by Letters Patent of the United States is:

1. A bone reamer, comprising:
    a shaft with a longitudinal axis, a proximal end and a distal end; and
    a cutting head provided at the distal end of the shaft, the cutting head having a configuration of half a hemisphere and having a shape of a shell having a logarithmic spiral, the cutting head being provided with a plurality of spokes configured to cut bone by extending radially away from the shaft to a continuous base of the cutting head the base connecting distal regions of all of the plurality of spokes, and in a direction perpendicular to the longitudinal axis of the shaft, wherein each of the plurality of spokes has a radius defined as the length of the spoke between the longitudinal axis of the shaft and the base of the cutting head wherein the radius of each of the plurality of spokes is different from the radius of an adjacent spoke, and wherein the longitudinal axis of the shaft is radially offset from the base of the cutting head.

2. The reamer of claim 1, wherein the shaft is fully cannulated to allow a surgical instrument to pass therethrough.

3. The reamer of claim 1, wherein both the shaft and the cutting head are fully cannulated.

4. The reamer of claim 1, wherein each of the plurality of spokes has a cutting edge for forming a bone socket.

5. The reamer of claim 1, wherein the proximal end is provided with a connecting system for mating with a power tool.

6. The reamer of claim 1, further comprising a drill tip adjacent the cutting head, the cutting head being disposed between the drill tip and the shaft.

7. The reamer of claim 6, wherein the drill tip, the cutting head and the shaft are fully cannulated to allow a drill pin to pass therethrough.

8. The reamer of claim 7, further comprising a securing and capturing mechanism including a clamping or chuck mechanism coupled to a pin, wherein the pin is inserted and captured within the cannulation of the shaft, to close the cannulation and provide stability of the reamer when the reamer is not employed with a drill pin.

9. The reamer of claim 6, wherein the drill tip is integral to the cutting head.

10. The reamer of claim 6, wherein the drill tip is removably attached to and detached from the cutting head.

11. The reamer of claim 1, wherein the cutting head is provided with a separate detachable nub or peg located in a center of the cutting head.

12. The reamer of claim 1, wherein each of the plurality of spokes has a length different from all lengths of remaining spokes.

* * * * *